Figure 1:
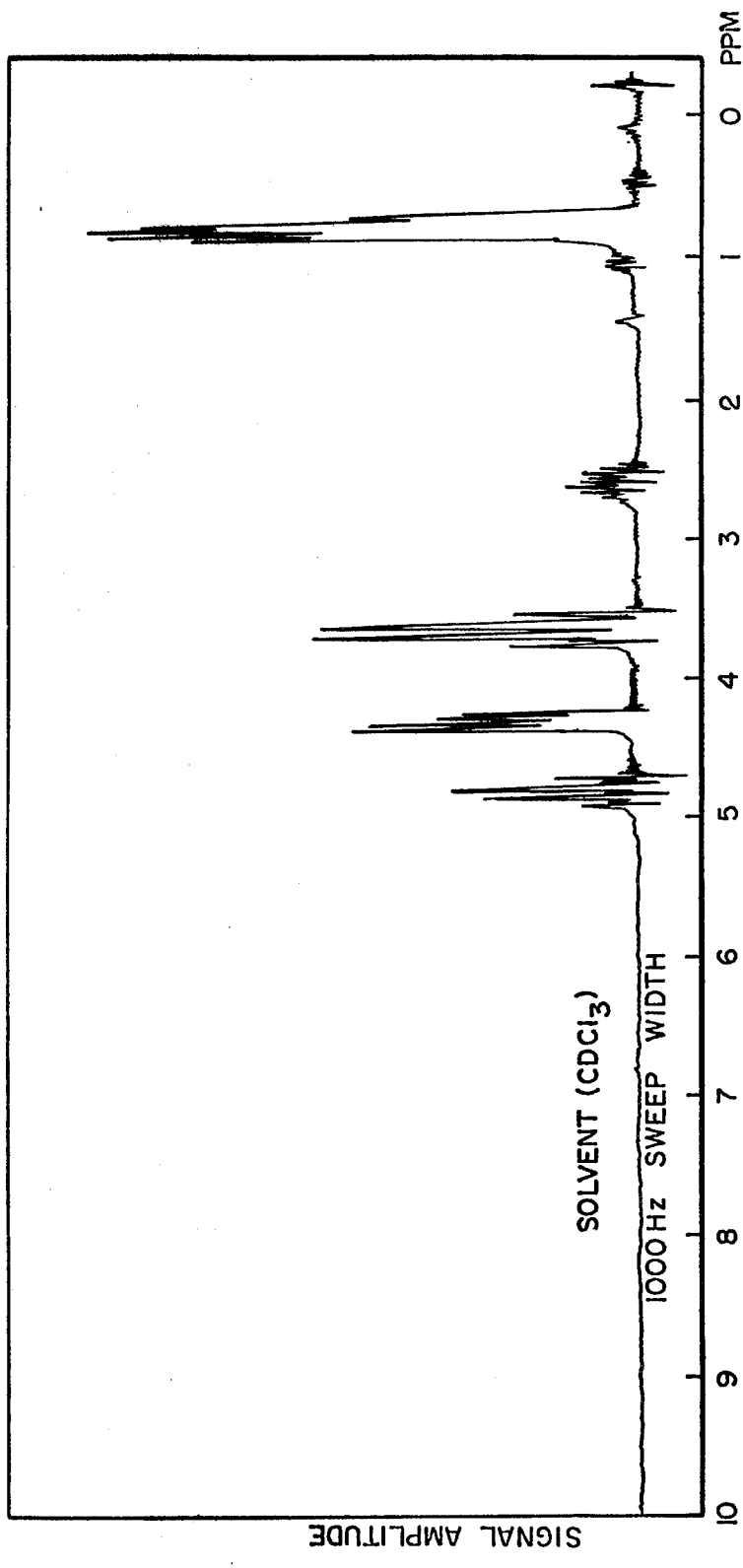

United States Patent [19]

Hall et al.

[11] 4,094,823
[45] June 13, 1978

[54] ETHYL-2-METHYL-3,4-PENTADIENOATE PERFUME COMPOSITIONS

[75] Inventors: John B. Hall, Rumson; Denis E. Hruza, Brick Town; Manfred Hugo Vock, Locust; Joaquin Vinals, Red Bank, all of N.J.; Edward J. Shuster, Brooklyn, N.Y.

[73] Assignee: International Flavors & Fragrances Inc., New York, N.Y.

[21] Appl. No.: 683,330

[22] Filed: May 5, 1976

Related U.S. Application Data

[62] Division of Ser. No. 566,118, Apr. 8, 1975, Pat. No. 3,978,239.

[51] Int. Cl.² .................................................. C11B 9/00
[52] U.S. Cl. ................................. 252/522; 260/405.5; 560/205
[58] Field of Search .................... 252/522; 260/486 R, 260/405.5

[56] References Cited

U.S. PATENT DOCUMENTS

| | | | |
|---|---|---|---|
| 3,225,102 | 12/1965 | Thompson | 260/598 |
| 3,236,869 | 2/1966 | Thompson | 260/405.5 |
| 3,743,657 | 7/1973 | Watanabe et al. | 260/486 R |

FOREIGN PATENT DOCUMENTS

| | | | |
|---|---|---|---|
| 2,119,580 | 7/1972 | France | 252/522 |

*Primary Examiner*—Veronica O'Keefe
*Attorney, Agent, or Firm*—Arthur L. Liberman; Franklin D. Wolffe

[57] ABSTRACT

Described are methods for preparing foodstuffs, flavoring compositions for foodstuffs, tobacco compositions, flavoring compositions for tobacco, perfume compositions, ingredients for perfume compositions, perfumed articles and ingredients for perfumed articles by including therein one or more $C_1$-$C_6$ alkyl-2-methyl-3,4-pentadienoates in order to produce:

(a) In food flavorings, sweet, fruity, winey, strawberry, tagette oil-like, pear and/or apple-like aromas and sweet, fruity, winey, creamy, strawberry, tagette oil-like, pear and/or apple tastes;

(b) In perfumes, berry, chamomile, wormwood, apple and/or pineapple notes; and (c) In tobaccos, sweet, woody and/or fruity notes;

as well as the novel compounds, isobutyl-2-methyl-3,4-pentadienoate and n-hexyl-2-methyl-3,4-pentadienoate.

3 Claims, 6 Drawing Figures

EXAMPLE I, FRACTION 10 Ethyl-2-methyl-3,4-pentadienoate

EXAMPLE I, FRACTION 10 Ethyl-2-methyl-3,4-pentadienoate

EXAMPLE I, FRACTION 10  Ethyl-2-methyl-3,4-pentadienoate

EXAMPLE XIX  Hexyl-2-methyl-3,4-pentadienoate

EXAMPLE XIX, Hexyl-2-methyl-3,4-pentadienoate

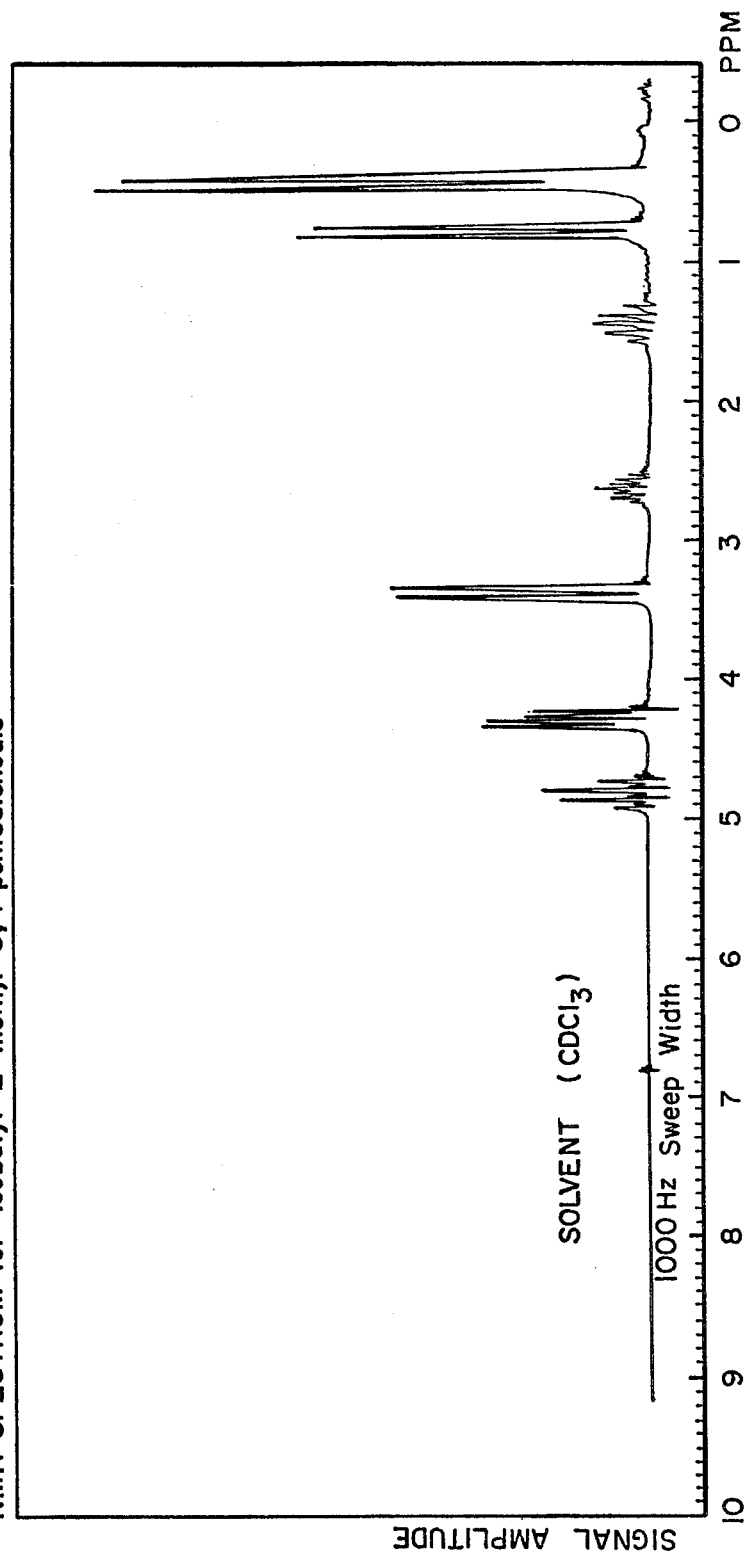

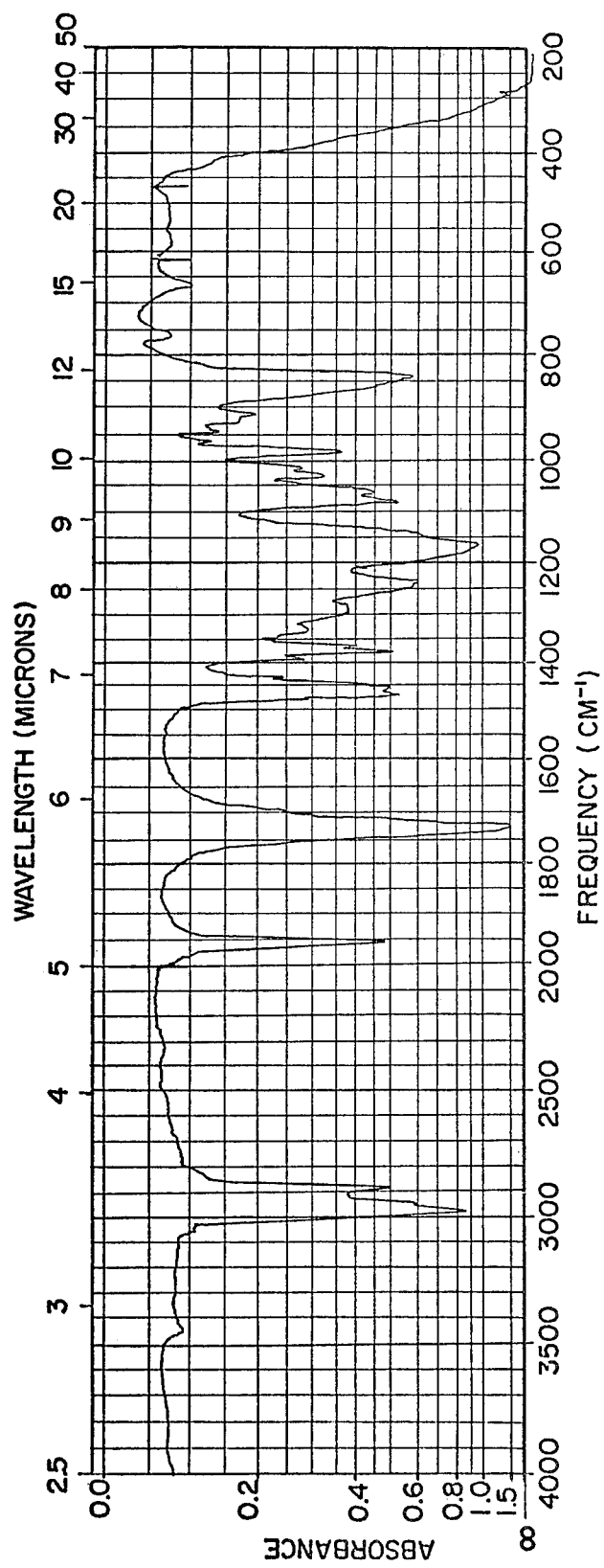
FIG. 6 EXAMPLE XXVI
INFRA RED SPECTRUM for Isobutyl-2-methyl-3,4-pentadienoate

ETHYL-2-METHYL-3,4-PENTADIENOATE PERFUME COMPOSITIONS

This application is a divisional application of U.S. application for patent Ser. No. 566,118, filed on Apr. 8, 1975, now U.S. Pat. No. 3,978,239 issued on Aug. 31, 1976.

BACKGROUND OF THE INVENTION

The present invention relates to $C_1$-$C_6$ alkyl-2-methyl-3,4-pentadienoates, more particularly isobutyl-2-methyl-3,4-pentadienoate and n-hexyl-2-methyl-3,4-pentadienoate to alter the flavor and/or aroma of consumable materials, e.g., tobacco, foodstuffs, perfume compositions and perfumed articles.

There has been considerable work performed related to substances which can be used to impart (or enhance) flavors to (or in) various consumable materials. These substances are used to diminish the use of natural materials, some of which may be in short supply and to provide more uniform properties in the finished product. Sweet, fruity, winey, pear, strawberry, tagette oil-like and apple aromas as well as sweet, fruity, winey, strawberry, creamy, tagette oil-like, apple and pear tastes are particularly desirable for many uses in foodstuff flavors. Chamomile, fruity, wormwood and strawberry notes are desirable in perfume compositions. Fruity, sweet and woody notes are desirable in tobacco flavoring compositions.

U.S. Pat. No. 3,499,769 issued on Mar. 10, 1970 discloses processes for imparting a fresh fruity flavor (particularly strawberry flavor) to foods by adding a small amount of 2-methyl-2-pentenoic acid to the foodstuff. In U.S. Pat. No. 3,499,769 it is emphasized that the basic nuance imparted by 2-methyl-2-pentenoic acid is a "berry" flavor. Quite unexpectedly, the novel compositions of matter of the instant invention have properties different in kind from the 2-methyl-2-pentenoic acid of U.S. Pat. No. 3,499,769.

Methyl-2-methyl-3,4-pentadienoate and ethyl-2-methyl-3,4-pentadienoate are known compounds, but uses of these compounds taking advantage of their organoleptic properties, in foodstuffs, perfume compositions, perfumed articles and/or tobacco are not disclosed in the prior art.

Synthesis of ethyl-2-methyl-3,4-pentadienoate by means of reaction of propargyl alcohol with triethyl orthopropionate is disclosed by Crandall and Tindell, J. Chem. Soc. D 1970 (21), 1411–12.

Synthesis of methyl-2-methyl-3,4-pentadienoate by means of reaction of 3,4-pentadienoic acid with $CH_2N_2$ ($C_2H_5$)$_2$O is disclosed by Ullman and Fanshawe, J. Am. Chem. Soc. 83, 2379–83 (1961).

Japanese Patent J75000022 (Tanabe Seiyaku Co. Ltd.) discloses aryl-alkyl 1,3-pentadiene-1-carboxylates useful as deodorants and antibacterial agents of the formula:

$$CH_3-CH=CH-CH=CH-C(O)-O(CH_2)_nR$$

(where R is phenyl, alkylphenyl, alkoxyphenyl, dialkylamino phenyl or methylenedioxyphenyl, n is 1–3), as being prepared by condensing the corresponding acid with an aryl alkanol of the formula:

$$R(CH_2)_nOH$$

In addition, British Pat. No. 1,379,038 published on Jan. 2, 1975 includes a broad disclosure of γ, δ-unsaturated carbonyl compounds, useful as flavoring and odoriferous agents of the formula:

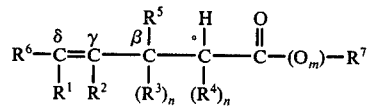

(where m is 0 or 1; n=0 and the dotted line is a bond or n=1 and the dotted line is no bond; $R^1$, $R^2$, $R^3$, $R^4$, $R^5$, $R^6$ and $R^7$ are each H, or linear or branched (a)cyclic, (un)saturated univalent hydrocarbon or oxygen-substituted hydrocarbon; or $R^7$ with $R^3$ or $R^4$ or $R^5$ may form a cycloaliphatic group, provided that $R^3$ and $R^5$ may not contain a multiple bond which is conjugated with the alpha, beta-bond) as being prepared by reacting an alphabeta-unsaturated carbonyl compound $(R^5)(R^3)_nC=C(C)-(O)_m-R^7$ or halogenated carbonyl compound $X(R^5)(R^3)_n-CH(R^4)_n-C(O)-R^7$ with an organometallic compound comprising a transition metal (preferred:Cu), an univalent cation (preferred:Li$^+$) or [Mg-Halogen]$^+$ and an alkenyl radical $R^6-C(R^1)=C(R^2)-$, preferred in the presence of a complexing agent e.g. diethyl ether, tetrahydrofuran, dimethoxyethane,N-tributylphosphine or trimethylphosphite.

THE INVENTION

It has now been discovered that solid and liquid foodstuff and flavoring compositions having sweet, winey, pear, strawberry, tagette oil-like and/or apple aromas and sweet, winey, strawberry, pear-like, tagette oil-like, apple-like and/or creamy taste notes; and novel perfume compositions having berry, acrid, apple, wormwood, chamomile and/or pineapple notes, as well as tobacco flavoring compositions capable of imparting a fruity and woody character to tobacco and tobacco articles, e.g., cigarettes and having aromatic, sweet and woody notes may be provided by the utilization of isomer mixtures containing one or more $C_1$-$C_6$ alkyl-2-methyl-3,4-pentadienoates.

The $C_1$-$C_6$ alkyl-2-methyl-3,4-pentadienoates useful in our invention are formed by reaction of propargyl alcohol and a tri-$C_1$-$C_6$ alkyl orthopropionate in the presence of a lower alkanoic acid according to the reaction:

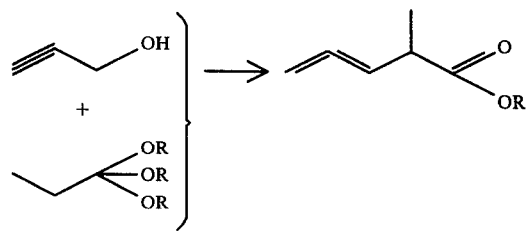

(wherein R is one of $C_1$-$C_6$ alkyl, e.g., methyl, ethyl, i-butyl or n-hexyl) at pressures of from 2 up to 10 atmospheres, and temperatures of 140°–180° C. The mole ratios of triethyl orthopropionate:propargyl alcohol may vary from 1:2 up to 2:1 with a slight molar excess of propargyl alcohol being preferred. The lower alkanoic acid present during the reaction may be any acetic acid, propionic acid, butyric acid, valeric acid or isovaleric acid.

When one or more of the $C_1$-$C_6$ alkyl-2-methyl-3,4-pentadienoates of our invention is used as a food flavor adjuvant, the nature of the co-ingredients included with the said $C_1$-$C_6$ alkyl-2-methyl-3,4-pentadienoates in formulating the product composition will also serve to alter the organoleptic characteristics of the ultimate foodstuff treated therewith. As used herein, in regard to flavors, the term "alter" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste". As used herein the term "foodstuff" includes both solids and liquids ingestible materials which usually do, but need not, have nutritional value. Thus, foodstuffs include soups, convenience foods, beverages, dairy products, candies, vegetables, cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches pectins, and emulsifiers, e.g., mono-and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts, such as ferric phosphate, ferrous gluconate and the like, riboflavon, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, 4-methylpentenoic acid, 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methyl butyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alpha-methylbutyrate, propyl acetate, amyl acetate, amyl butyrate, pentyl-2-methyl butyrate, benzyl salicylate, dimethyl anthranilate, ethyl methylphenylglycidate, ethyl succinate, isobutyl cinnamate, dimethyl benzyl carbinyl acetate, and terpenyl acetate; essential oils, such as jasmine absolute, rose absolute, oil of anise, orris absolute, lemon essential oil, Bulgarian rose, yara yara, natural raspberry oil and vanilla; lactones, sulfides, e.g., methyl sulfide and other materials such as maltol, acetoin, acetals (e.g., 1,1-diethoxyethane, 1,1-dimethoxyethane and dimethoxymethane), and hydrocarbons (e.g., 1-methyl naphthalene and 2-methyl naphthalene).

The specific flavoring adjuvant selected for use may be either solid or liquid depending upon the desired physical form of the ultimate product, i.e., foodstuff, whether simulated or natural, and should, in any event, be capable of providing an environment in which one or more of the $C_1$-$C_6$ alkyl-2-methyl-3,4-pentadienoates can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of $C_1$-$C_6$ alkyl-2-methyl-3,4-pentadienoates employed in a particular instance can vary over a relatively wide range whereby to its desired organoleptic effects having reference to the nature of the product are achieved. All parts and percentages given herein are by weight unless otherwise specified. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of $C_1-C_6$ alkyl-2-methyl-3,4-pentadienoates will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of one or more of the $C_1-C_6$ alkyl-2-methyl-3,4-pentadienoates ranging from a small but effective amount, e.g., 0.2 parts per million up to about 50 parts per million by weight based on total composition are suitable. Concentrations in excess of the maximum quantity stated are not normally recommended since they fail to prove commensurate enhancement of organoleptic properties. In those instances wherein the $C_1-C_6$ alkyl-2-methyl-3,4-pentadienoates is added to the foodstuff as an integral component of a flavoring composition, it is of course essential that the total quantity of flavoring composition employed be sufficient to yield an effective $C_1-C_6$ alkyl-2-methyl-3,4-pentadienoates concentration in the foodstuff product.

Food flavoring compositions prepared in accordance with the present invention preferably contain the $C_1-C_6$ alkyl-2-methyl-3,4-pentadienoates in concentrations ranging from about 0.015% up to about 10% by weight based on the total weight of said flavoring composition.

The compositions described herein can be prepared according to conventional techniques well known as typified by cake batters and fruit juices can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the $C_1-C_6$ alkyl-2-methyl-3,4-pentadienoates with for example gum arabic, gum tragacanth, carrageenan and the like, and thereafter spray-drying the resultant mixture whereby to obtain the particular solid product. Pre-prepared flavor mixes in powder form, e.g., a vanilla powder mix or a fruit flavored powder mix are obtained by mixing the dried solid components, e.g., starch, sugar and the like and $C_1-C_6$ alkyl-2-methyl-3,4-pentadienoates in a dry blender until the requisite degree of uniformity is achieved.

It is presently preferred to combine with one or more of the $C_1-C_6$ alkyl-2-methyl-3,4-pentadienoates the following adjuvants:
Ethyl heptanoate;
Geraniol;
Palatone;
Ethyl methyl phenyl glycidate;
Diacetyl;
Styralyl acetate;
Vanillin;
Ethyl vanillin;
Geranyl acetate;
Ethyl pelargonate;
Beta ionone;
Isoamyl acetate;
δ-Undecalactone;
Cuminic acetate;
Ethyl butyrate;
Gamma undecalactone;
Naphthyl ethyl ether;
Cinnamyl isobutyrate;
Oil of anise;
Ethyl acetate;
Ethyl laurate;
Amyl butyrate;
Isoamyl butyrate;
Ethyl decylate;
2-Methyl-2-pentenoic acid;
Elemecine (4-allyl-1,2,6-trimethoxy benzene);
Ethyl isobutyrate;
Isoelemecine (4-propenyl-1,2,6-trimethoxy benzene) and
Ethyl acetoacetate An additional aspect of our invention provides an organoleptically improved smoking tobacco product and additives thereof, as well as methods of making the same which overcome specific problems heretofore encountered in which specific desired sweet, fruity and woody flavor characteristics of natural tobacco are created or enhanced and may be readily controlled and maintained at the desired uniform level regardless of variations in the tobacco components of the blend.

This invention further provides improved tobacco additives and methods whereby various desirable sweet, fruity and woody flavoring characteristics may be imparted to smoking tobacco products and may be readily varied and controlled to produce the desired uniform flavoring characteristics.

In carrying out this aspect of our invention, we add to smoking tobacco materials of a suitable substitute therefor (e.g., dried lettuce leaves) or we add to filters for smoking tobacco articles (e.g., cellulose acetate filters) an aroma and flavor additive containing as an active ingredient one or more $C_1-C_6$ alkyl-2-methyl-3,4-pentadienoates.

In addition to the $C_1-C_6$ alkyl-2-methyl-3,4-pentadienoate of our invention other flavoring and aroma additives may be added to the smoking tobacco material or substitute therefor either separately or in mixture with the $C_1-C_6$ alkyl-2-methyl-3,4-pentadienoate as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1,2-methyl-5-isopropyl-1,3-nonadiene-8-one;
2,6-Dimethyl-2,6-undecadiene-10-one;

2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2,1-b)-furan;
4-Hydroxy hexanoic acid, gamma lactone;
Polyisoprenoid hydrocarbons defined in Example V of U.S. Pat. No. 3,589,372 issued on June 29, 1971.

II. Natural Oils

Celery seed oil;
Coffee extract;
Bergamot Oil;
Cocoa extract;
Nutmeg oil;
Origanum oil An aroma and flavoring concentrate containing one or more $C_1$-$C_6$ alkyl-2-methyl-3,4-pentadienoates and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substituents (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of one or more $C_1$-$C_6$ alkyl-2-methyl-3,4-pentadienoates to smoking tobacco material is between 5 ppm and 100 ppm (0.0005%–0.01%) of the active ingredients to the smoking tobacco material. We have further found that satisfactory results are obtained if the proportion by weight of the sum total of $C_1$-$C_6$ alkyl-2-methyl-3,4-pentadienoate used to flavoring material is between 50 and 1000 ppm (0.005%–0.1%).

Any convenient method for incorporating the $C_1$-$C_6$ alkyl-2-methyl-3,4-pentadienoate in the tobacco product may be employed. Thus, the $C_1$-$C_6$ alkyl-2-methyl-3,4-pentadienoate taken alone or along with other flavoring additives may be dissolved in a suitable solvent such as ethanol, pentane, diethyl ether and/or other volatile organic solvents and the resulting solution may either by spread on the cured, cased and blended tobacco material or the tobacco material may be dipped into such solution. Under certain circumstances, a solution of the $C_1$-$C_6$ alkyl-2-methyl-3,4-pentadienoate taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the $C_1$-$C_6$ alkyl-2-methyl-3,4-pentadienoate in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of ethyl-2-methyl-3,4-pentadienoate in an amount to provide a tobacco composition containing 20 ppm by weight of ethyl-2-methyl-3,4-pentadienoate on a dry basis. Thereafter, the alcohol is removed by evaporation and the tobacco is manufactured into cigarettes by the usual techniques. The cigarette when treated as indicated has a desired and pleasing sweet, fruity and woody aroma which is detectable in the main and side streams when the cigarette is smoked. This aroma is described as being sweeter, rich, less harsh, more tobacco-like and having woody, and fruity notes.

While our invention is particularly useful in the manufacture of smoking tobacco, such as cigarette tobacco, cigar tobacco and pipe tobacco, other tobacco products formed from sheeted tobacco dust or fines may also be used. Likewise, one or more $C_1$-$C_6$ alkyl-2-methyl-3,4-pentadienoates of our invention can be incorporated with materials such as filter tip materials, seam paste, packaging materials and the like which are used along with tobacco to form a product adapted for smoking. Furthermore, one or more $C_1$-$C_6$ alkyl-2-methyl-3,4-pentadienoates can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

One or more of the $C_1$-$C_6$ alkyl-2-methyl-3,4-pentadienoates and an auxiliary perfume ingredient, including, for example, alcohols, aldehydes, nitriles, esters, cyclic esters and natural essential oils, may be admixed so that the combined odors of the individual components produce a pleasant and desired fragrance, particularly and preferably in strawberry fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual components will contribute its particular olfactory characteristics, but the over-all effect of the perfume composition will be the sum of the effects of each of the ingredients. Thus, one or more of the $C_1$-$C_6$ alkyl-2-methyl-3,4-pentadienoates can be used to alter the aroma characteristics of a perfume composition, for example, by utilizing or moderating the olfactory reaction contributed by another ingredient in the composition.

The amount of $C_1$-$C_6$ alkyl-2-methyl-3,4-pentadienoate of our invention which will be effective in perfume compositions depends on many factors, including the other ingredients, their amounts and the effects which are desired. It has been found that perfume compositions containing as little as 0.3% of $C_1$-$C_6$ alkyl-2-methyl-3,4-pentadienoate or even less (e.g., 0.05%) can be used to impart a scent odor to soaps, cosmetics or other products. The amount employed can range up to 5% of the fragrance components and will depend on considerations of cost, nature of the end product, the effect desired on the finished product and the particular fragrance sought.

The $C_1$-$C_6$ alkyl-2-methyl-3,4-pentadienoate is useful in perfume compositions as an olfactory component in detergents and soaps, space odorants and deodorants, perfumes, colognes, toilet waters, bath preparations, such as bath oils, and bath solids; hair preparations, such as lacquers, brilliantines, pomades and shampoo; cosmetic preparations, such as creams, deodorants, hand lotions and sun screens; powders, such as talcs, dusting powders, face powders and the like. When used as an olfactory component of a perfumed article, as little as 100 parts per million of $C_1$-$C_6$ alkyl-2-methyl-3,4-pentadienoate will suffice to impart a fruity, acrid, strawberry character which is one of the key odor characteristics of strawberry perfume formulations. Generally, no more than 2.0% of one or more $C_1$-$C_6$ alkyl-2-methyl-3,4-pentadienoates based on the ultimate end product is required in the perfume composition.

In addition, the perfume composition or fragrance composition of our invention can contain a vehicle, or carrier for the $C_1$-$C_6$ alkyl-2-methyl-3,4-pentadienoate. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that one or more $C_1$-$C_6$ alkyl-2-methyl-3,4-pentadienoates can be utilized to alter the sensory properties, particularly organoleptic properties, such as flavor and/or fragrance of a wide variety of consumable materials.

The following examples are given to illustrate embodiments of the invention as it is presently preferred to practice it. It will be understood that these examples are illustrative, and the invention is not to be considered as restricted thereto except as indicated in the appended claims.

EXAMPLE I

PREPARATION OF ETHYL-2-METHYL-3,4-PENTADIENOATE

Reaction:

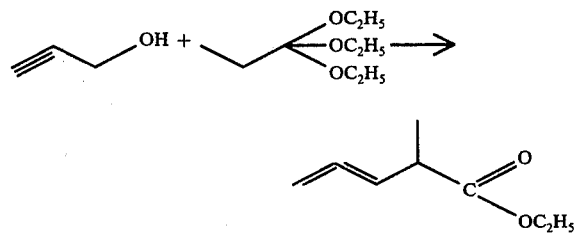

Into a 2 liter autoclave, the following materials are placed:

| Ingredient | Amount |
|---|---|
| Triethyl orthopropionate | 495 grams |
| 2-Propyn-1-ol | 90 grams |
| Propionic acid | 12 grams |

The autoclave is closed and the reaction mass is heated to 150° C. over a period of 50 minutes. The reaction mass is then maintained at a temperature of between 135°–160° C and at a pressure of 20 up to 60 psig for a period of 3 hours. At the end of this 3-hour period, the autoclave is opened and the reaction mass is cooled to room temperature. 12.6 g of sodium bicarbonate is then added to the reaction mass in order to neutralize the propionic acid. 30 g of Primol ® (see note 1) and 0.1 g of Ionol[R] (see note 2) are added and the resulting reaction product is fractionally distilled at atmospheric pressure to a pot temperature of 129° C. A mixture of ethanol and ethyl propionate is distilled over. Vacuum is then applied to the distillation column and the resultant product, ethyl-2-methyl-3,4-pentadienoate is distilled at a vapor temperature of 65°–69° C at a pressure of 24–33 mm Hg as fractions 5–10 of the following fractions:

| Fraction No. | Vapor Temperature | Liquid Temperature | Pressure (mm Hg) | Weight of Fraction | Reflux Ratio |
|---|---|---|---|---|---|
| 1 | 68–72° C | 127–87° C | 760 | 174.5 g | 9:1 |
| 2 | 28–42 | 86–83 | 48–50 | 19.4 | 9:1 |
| 3 | 69 | 84 | 45 | 12.6 | 9:1 |
| 4 | 65 | 79 | 34 | 20.1 | 9:1 |
| 5 | 67 | 80 | 33 | 38.9 | 4:1 |
| 6 | 67 | 82 | 33 | 32.5 | 4:1 |
| 7 | 67 | 82 | 33 | 36.8 | 4:1 |
| 8 | 67 | 83 | 33 | 37.2 | 4:1 |
| 9 | 66 | 84 | 24 | 39.8 | 4:1 |
| 10 | 65 | 94 | 24 | 36.9 | 4:1 |
| 11 | 57 | 108 | 10 | 45.5 | 4:1 |
| 12 | 39 | 172 | 2.3 | 14.5 | 4:1 |

The resulting material is confirmed by IR, NMR and mass spectral analyses to have the structure:

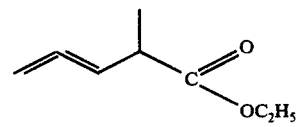

Mass spectral analysis

Parent peak, then in order of decreasing intensity: m/e = 140(M+); 67, 97, 29, 41, 125

Nuclear Magnetic Resonance Analysis:

| ppm | Interpretation | |
|---|---|---|
| 1.26 ppm (t) | $CH_3-C-O-C-$ with $\|O$ | 6H |
| 1.28 ppm (d) | $CH_3-C-C-$ with $\|O$ | 6H |
| 3.10 ppm (m) | $=C-CH-C=O$ | 1H |
| 4.12 ppm (q) | $CH_3-CH_2-O-C-$ with $\|O$ | 2H |
| 4.76 ppm (m) | $H_2C=C=C-$ | 2H |
| 5.40 ppm (m) | $C=C=CH$ | 1H |

The nuclear magnetic resonance spectrum is set forth in FIG. 1.

Infra Red Analysis

Peaks 850 cm$^{-1}$
1050
1175
1225
1375
1425
1730
1950
2880
2925
2975

Figure 2:
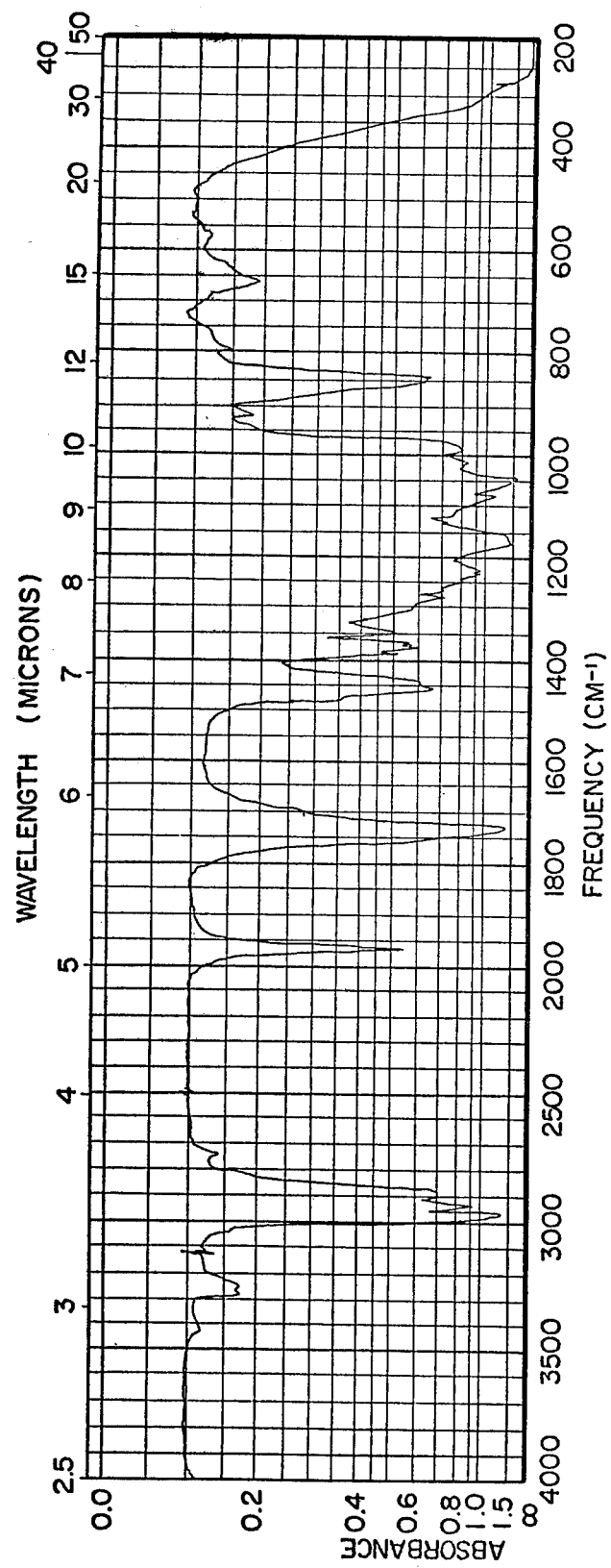

The infra-red spectrum is set forth in FIG. 2.

At a concentration of 0.5 ppm, the resulting product, ethyl-2-methyl-3,4-pentadienoate has a fruity, strawberry, creamy aroma with berry, apple and pineapple notes and a sweet, fruity, strawberry flavor with woody and creamy nuances.

Note 1: Primol ® is a registered trademark identifying a hydrocarbon mineral oil produced by Exxon Corp. of Linden, New Jersey.

Note 2: Ionol ® is a registered trademark identifying the compound 2,6-di-t-butyl-4-methyl phenol.

EXAMPLE II

PREPARATION OF ETHYL-2-METHYL-3,4-PENTADIENOATE

Reaction:

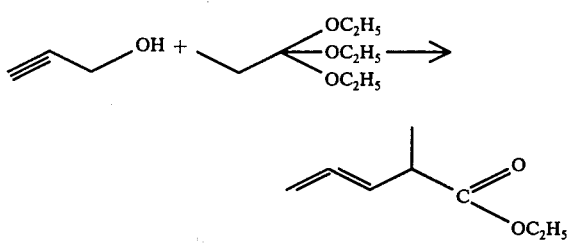

Into a 2 liter autoclave, the following materials are placed:

| Ingredient | Amount |
| --- | --- |
| Triethyl orthopropionate | 880 grams (5 moles) |
| 2-Propyn-1-ol | 336 grams (6 moles) |
| Propionic acid | 25 grams |

The autoclave is closed and the reaction mass is heated to 160° C over a period of 50 minutes. The reaction mass is maintained at a temperature of between 150°–160° C and at a pressure of 40 up to 90 psig for a period of 3 hours. At the end of this 3-hour period, the autoclave is opened and the reaction mass is cooled to room temperature. 25.0 g of sodium bicarbonate is then added to the reaction mass in order to neutralize the propionic acid. 30 g of Primol ® and 0.1 g of Ionol ® are added and the resulting reaction product is distilled in a "rush-over" column yielding the following fractions:

| Fraction No. | Vapor Temperature | Liquid Temperature | Pressure (mm Hg) | Weight of Fraction |
| --- | --- | --- | --- | --- |
| 1 | 37–39° C | 41–43° C | 100 | 171.0 g |
| 2 | 42 | 47 | 100 | 165.3 |
| 3 | 47 | 58 | 100 | 137.6 |
| 4 | 82 | 98 | 100 | 179.3 |
| 5 | 114 | 113 | 100 | 203.4 |
| 6 | 120 | 150 | 100 | 217.3 |
| 7 | 75 | 200 | 100 | 13.7 |

Fractions 2–4 are combined; and 20 g Primol ® and 1 g Ionol ® are added thereto. The resulting mixture is distilled in a 1 foot × 1 inch Goodloe distillation column, yielding the following fractions:

| Fraction No. | Vapor Temperature | Liquid Temperature | Pressure (mm Hg) | Reflux Ratio | Weight of Fraction |
| --- | --- | --- | --- | --- | --- |
| 1 | 35–104° C | 102–110° C | 120 | 19:1 | 24.1 g |
| 2 | 104 | 110 | 120 | 9:1 | 6.6 |
| 3 | 104 | 110 | 120 | 9:1 | 6.1 |
| 4 | 104 | 110 | 120 | 9:1 | 21.1 |
| 5 | 105 | 111 | 120 | 9:1 | 18.6 |
| 6 | 105 | 111 | 120 | 9:1 | 18.7 |
| 7 | 105 | 111 | 120 | 9:1 | 16.7 |
| 8 | 105 | 112 | 120 | 9:1 | 19.3 |
| 9 | 105 | 112 | 120 | 9:1 | 21.4 |
| 10 | 105 | 112 | 120 | 9:1 | 15.8 |
| 11 | 104–105 | 112 | 120 | 9:1 | 25.1 |
| 12 | 105 | 113 | 120 | 9:1 | 25.0 |
| 13 | 105 | 114 | 120 | 9:1 | 21.4 |
| 14 | 105 | 115 | 120 | 9:1 | 23.0 |
| 15 | 105 | 117 | 120 | 9:1 | 23.8 |
| 16 | 105 | 121 | 120 | 9:1 | 27.6 |
| 17 | 105 | 130 | 120 | 9:1 | 28.7 |
| 18 | 105 | 172 | 120 | 9:1 | 28.5 |
| 19 | 107 | 181 | 120 | 9:1 | 11.2 |
| 20 | 108 | 210 | 120 | 9:1 | 8.9 |

Fractions 9–18 are combined and confirmed to by IR, NMR and mass spectral analyses to be ethyl-2-methyl-3,4-pentadienoate, having the structure:

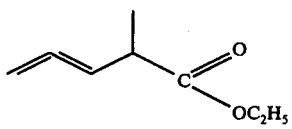

The mass spectral analysis, nuclear magnetic resonance spectrum and infrared spectrum are identical to those set forth in Example I and in FIGS. 1 and 2. At a concentration of 0.2 ppm, the resulting product, ethyl-2-methyl-3,4-pentadienoate has a fruity, strawberry, creamy aroma with berry, apple and pineapple notes and a sweet, fruity, strawberry flavor with woody and creamy nuances.

EXAMPLE III

FLAVOR FORMULATION CONTAINING ETHYL-2-METHYL-3,4-PENTADIENOATE

The following basic strawberry formulation is prepared:

| Ingredient | Parts by Weight |
| --- | --- |
| Parahydroxy benzyl acetone | 5 |
| Vanillin | 15 |
| Maltol | 20 |
| Ethyl-3-methyl-3-phenyl glycidate | 15 |
| Ethyl acetate | 13 |
| Ethyl butyrate | 20 |
| Methyl cinnamate | 5 |
| Methyl anthranilate | 1 |
| Ethyl benzoate | 1 |
| Gamma undecalactone | 2 |
| Diacetyl | 2 |
| Anethole | 1 |
| Cis-3-hexenol | 20 |
| 95% aqueous ethanol | 180 |
| Propylene glycol | 700 |
| | 1000 |

To a portion of the foregoing formulation, 4% by weight of ethyl-2-methyl-3,4-pentadienoate prepared according to the process of Example I is added. The formulation with the ethyl-2-methyl-3,4-pentadienoate is compared to the same formulation without said ethyl-2-methyl-3,4-pentadienoate.

Both flavors are evaluated in water at the rate of 50 ppm. Both beverages are tasted by an expert panel. The beverage containing the strawberry formulation with the addition of ethyl-2-methyl-3,4-pentadienoate is unanimously preferred as having fresh strawberry and a sweet-strawberry aroma and taste missing in the basic strawberry formulation.

EXAMPLE IV

TOBACCO FLAVOR FORMULATION AND TOBACCO

A tobacco mixture is produced by admixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes having cellulose acetate filters are prepared from this tobacco.

The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. One-third of the cigarettes are then treated in the tobacco section thereof with 5 ppm of ethyl-2-methyl-3,4-pentadienoate produced according to the process of Example II. One-third of the cigarettes are treated on the cellulose acetate filter with 1 microliter of a 0.1% ethanol solution of ethyl-2-methyl-3,4-pentadienoate produced according to Example II.

The control cigarettes not containing the mixture having any ethyl-2-methyl-3,4-pentadienoate produced according to the process of Example II and the experimental cigarettes which do contain ethyl-2-methyl-3,4-pentadieonate produced according to the process of Example II are evaluated by three-way comparison, and the results are as follows:

In aroma, the cigarettes containing the ethyl-2-methyl-3,4-pentadienoate in the tobacco or in the filter have been found to be sweeter and fruitier.

In smoke flavor, the cigarettes containing the ethyl-2-methyl-3,4-pentadienoate are more aromatic, more sweet, fruitier and slightly less harsh in the mouth and throat. In addition, those cigarettes containing the ethyl-2-methyl-3,4-pentadienoate in the tobacco give rise to a woody nuance in the taste and aroma in smoking.

EXAMPLE V

STRAWBERRY FRAGRANCE

The following mixture is prepared:

| Ingredient | Parts by Weight |
| --- | --- |
| Cuminic acetate | 15 |
| Ethyl acetoacetate | 3 |
| Ethyl laurate | 30 |
| Cinnamyl isobutyrate | 15 |
| Cinnamyl decylate | 20 |
| Diacetyl (10% in 95% aqueous ethanol) | 2 |
| Ethyl pelargonate | 5 |
| Gamma undecalactone | 20 |
| Ethyl isobutyrate | 110 |
| Ethyl isovalerate | 60 |
| Ethyl heptanoate | 12 |
| Dulcinyl | 5 |
| 2(para-hydroxyphenyl)-3-butanone | 2 |
| Ethyl acetate | 5 |
| Beta-ionone | 5 |
| Palatone | 3 |
| Vanillin | 10 |
| Ethyl vanillin | 10 |
| Ethyl-3-methyl-3-phenyl glycidate | 70 |
| Ethyl-2-methyl-3,4-pentadienoate prepared according to the process of Example II | 10 |

The mixture containing ethyl-2-methyl-3,4-pentadienoate prepared according to the process of Example II imparts the slight acrid, berry undertone necessary to the strawberry aroma.

EXAMPLE VI

PREPARATION OF SOAP COMPOSITION

One hundred grams of soap chips are mixed with one gram of the perfume composition of Example V until a substantially homogeneous composition is obtained. The perfumed soap composition manifests an excellent strawberry character with a berry undertone.

EXAMPLE VII

PREPARATION OF A DETERGENT COMPOSITION

A total of 100 g of a detergent powder is mixed with 0.15 g of the perfume composition of Example V until a substantially homogeneous composition is obtained. This composition has an excellent strawberry fragrance.

EXAMPLE VIII

PREPARATION OF A COSMETIC POWDER COMPOSITION

A cosmetic powder is prepared by mixing in a ball mill, 100 g of talcum powder with 0.25 g of the ethyl-2-methyl-3,4-pentadienoate prepared according to Example II. It has an excellent fruity, strawberry aroma with a creamy nuance.

EXAMPLE IX

PERFUMED LIQUID DETERGENT

Concentrated liquid detergents with a fruity, strawberry odor are prepared containing 0.10%, 0.15% and 0.20% of ethyl-2-methyl-3,4-pentadienoate prepared according to Example II. They are prepared by adding and homogeneously mixing the appropriate quantity of ethyl-2-methyl-3,4-pentadienoate in the liquid detergent. The detergents all possess a fruity, strawberry fragrance, the intensity increasing with greater concentrations of ethyl-2-methyl-3,4-pentadienoate.

EXAMPLE X

PREPARATION OF A COLOGNE AND HANDKERCHIEF PERFUME

The composition of Example V is incorporated in a cologne at a concentration of 2.5% in 85% aqueous ethanol; and into a handkerchief perfume at a concentration of 20% (in 95% aqueous ethanol). The use of the mixture containing ethyl-2-methyl-3,4-pentadienoate in the composition of Example V affords a distinct and definite strong strawberry aroma with a fruity note to the handkerchief perfume and cologne.

EXAMPLE XI

PREPARATION OF SOAP COMPOSITION

One hundred grams of soap chips are mixed with one gram of ethyl-2-methyl-3,4-pentadienoate produced according to Example II until a substantially homogeneous composition is obtained. The perfumed soap composition manifests an excellent strawberry aroma with a fruity note.

EXAMPLE XII

PREPARATION OF A DETERGENT COMPOSITION

A total of 100 g of a detergent powder is mixed with 0.15 g of the mixture containing ethyl-2-methyl-3,4-pentadienoate of Example I until a substantially homogeneous composition is obtained. This composition has an excellent strawberry aroma with a fruity note.

EXAMPLE XIII

The following concentrate is prepared:

| Ingredient | Parts by Weight |
| --- | --- |
| Geraniol | 1.00 |
| Ethyl methyl phenyl glycidate | 3.33 |
| Ethyl-2-methyl-3,4-pentadienoate (prepared according to the process of Example I) | 4.77 |
| Vanillin | 5.66 |
| Ethyl pelargonate | 13.06 |
| Isoamyl acetate | 14.00 |
| Ethyl butyrate | 58.18 |

EXAMPLE XIV

Another concentrate is prepared as follows:

| Ingredient | Parts by Weight |
| --- | --- |
| Naphthyl ethyl ether | 0.96 |
| Vanillin | 2.66 |
| Ethyl methyl phenyl glycidate | 2.88 |
| Ethyl-2-methyl-3,4-pentadienoate (prepared according to the process of Example I) | 4.90 |
| Ethyl acetate | 9.58 |
| Isoamyl acetate | 12.25 |
| Ethyl butyrate | 26.20 |
| Isoamyl butyrate | 40.57 |

EXAMPLE XV

The concentrate prepared in Example XIII is dissolved in 4 volumes of propylene glycol and the mixture is added to a hard candy melt at the rate of 1.5 oz of the concentrate solution per 100 lbs. of melt. After the finished candy has been produced, it is found to have an excellent strawberry flavor. When the candy is compared with candy made under the same conditions, but without the ethyl-2-methyl-3,4-pentadienoate prepared according to the process of Example I in the concentrate, it is found to have an inferior strawberry flavor.

EXAMPLE XVI

The propylene glycol solution of the concentrate as prepared in Example XV is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the ethyl-2-methyl-3,4-pentadienoate prepared according to the process of Example I

EXAMPLE XVII

The flavor concentrate prepared in Example XIV is admixed with gum arabic and in the production of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the ethyl-2-methyl-3,4-pentadienoate prepared according to the process of Example II in the concentrate.

EXAMPLE XIX

(A) PREPARATION OF TRIHEXYL-ORTHOPROPIONATE

Reaction:

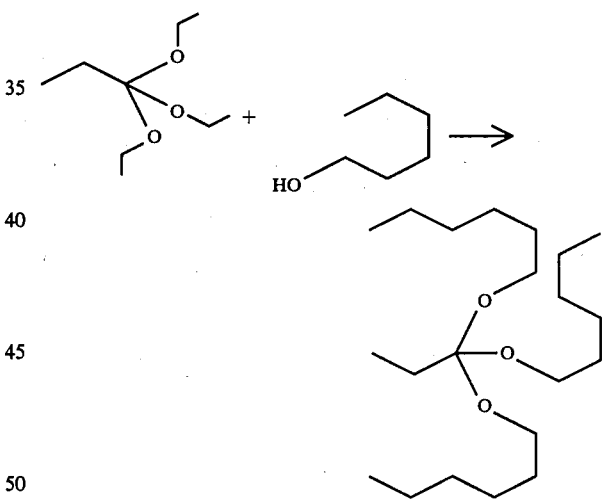

Into a three-liter distillation flask, equipped with a 2 inch splash column, reflux condenser and fraction cutter, the following materials are placed:

| Ingredients | Amount |
| --- | --- |
| Triethyl ortho propionate | 528 g (3 moles) |
| n-Hexyl alcohol | 1530 g (15 moles) |
| p-Toluene sulfonic acid | 3.4 g (0.02 moles) |
| Primol ® | 20 g |

The reaction mass is heated to a pot temperature of 150° C at atmospheric pressure and 398.9 g of "light" (ethanol) fractions distills off. The reaction mass is then placed under vacuum and the reaction product is distilled over as a colorless liquid at 1.3 mm Hg pressure and a temperature of 140°–171° C. The yield is 930.7 g (87.6%) and the product is a compound having the structure:

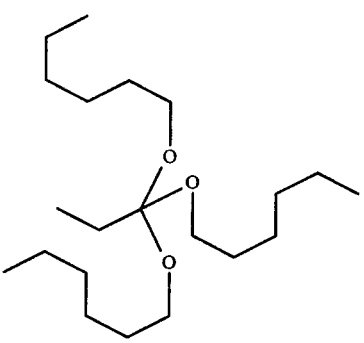

(B) PREPARATION OF n-HEXYL-2-METHYL-3,4-PENTADIENOATE

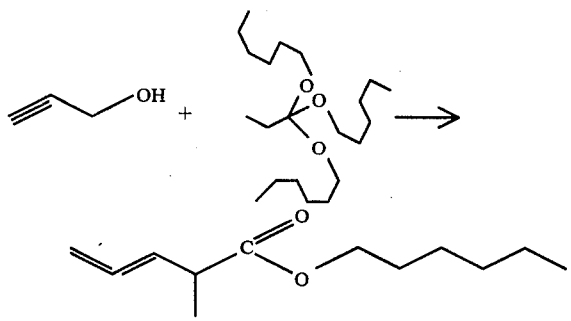

Into a 2-liter autoclave, the following materials are placed:

| Ingredient | Amount |
|---|---|
| n-Hexyl orthopropionate (produced according to the process of Part A) | 1240 grams (3.5 moles) |
| 2-Propyn-1-ol | 196 grams (3.5 moles) |
| Propionic acid | 30 grams |

The autoclave is closed and the reaction mass is heated to 120°–130° C (a heatup time of 50 minutes). The reaction mass is maintained at a temperature of between 120°–130° C for a period of 5 hours. At the end of this 5-hour period, the autoclave is opened and the reaction mass is cooled to room temperature. 35 g of sodium bicarbonate is then added to the reaction mass in order to neutralize the propionic acid. 40 g of Primol $^R$ is added and the resulting reaction product is distilled to yield ten fractions. Fractions 6, 7 and 8 distilling 95°–101° C and 2.2–2.5 mm Hg (to yield 481.3 g of a crude product) are combined and fractionally distilled on a 12 inch × 1 inch Goodloe column after adding thereto 10.0 g Primol $^R$ and 0.1 g Ionol ®, as follows:

| Fraction No. | Vapor Temperature | Liquid Temperature | Pressure (mm Hg) | Weight of Fraction | Reflux Ratio |
|---|---|---|---|---|---|
| 1 | 44 | 72–87 | 3.5–3.4 | 40.0 g | 9:1 |
| 2 | 47 | 97 | 3.4 | 33.9 | 9:1 |
| 3 | 77 | 101 | 3.4 | 36.5 | 9:1 |

-continued

| Fraction No. | Vapor Temperature | Liquid Temperature | Pressure (mm Hg) | Weight of Fraction | Reflux Ratio |
|---|---|---|---|---|---|
| 4 | 88 | 104 | 3.4 | 20.3 | 9:1 |
| 5 | 89 | 104 | 3.4 | 33.9 | 9:1 |
| 6 | 89 | 104 | 3.4 | 29.1 | 9:1 |
| 7 | 80–89 | 105–115 | 3.5–3.4 | 33.5 | 9:1 |
| 8 | 89 | 115 | 3.2 | 33.4 | 9:1 |
| 9 | 89 | 117 | 3.1 | 84.1 | 3:1 |
| 10 | 90 | 119 | 3.2 | 83.6 | 3:1 |
| 11 | 86–89 | 110–112 | 3.2 | 32.5 | 9:1 |
| 12 | 89 | 125 | 3.2 | 74.4 | 3:1 |
| 13 | 88 | 155 | 3.3 | 32.4 | 3:1 |
| 14 | 110 | 195 | 3.3 | 44.5 | 3:1 |

The resulting material is confirmed by IR, NMR and mass spectral analyses to have the structure:

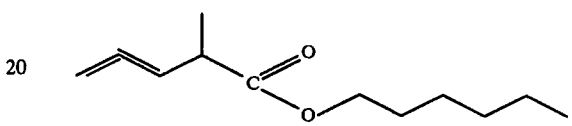

It has a tagette-oil-like, apple taste and aroma with pear and fatty nuances.

Figure 3:
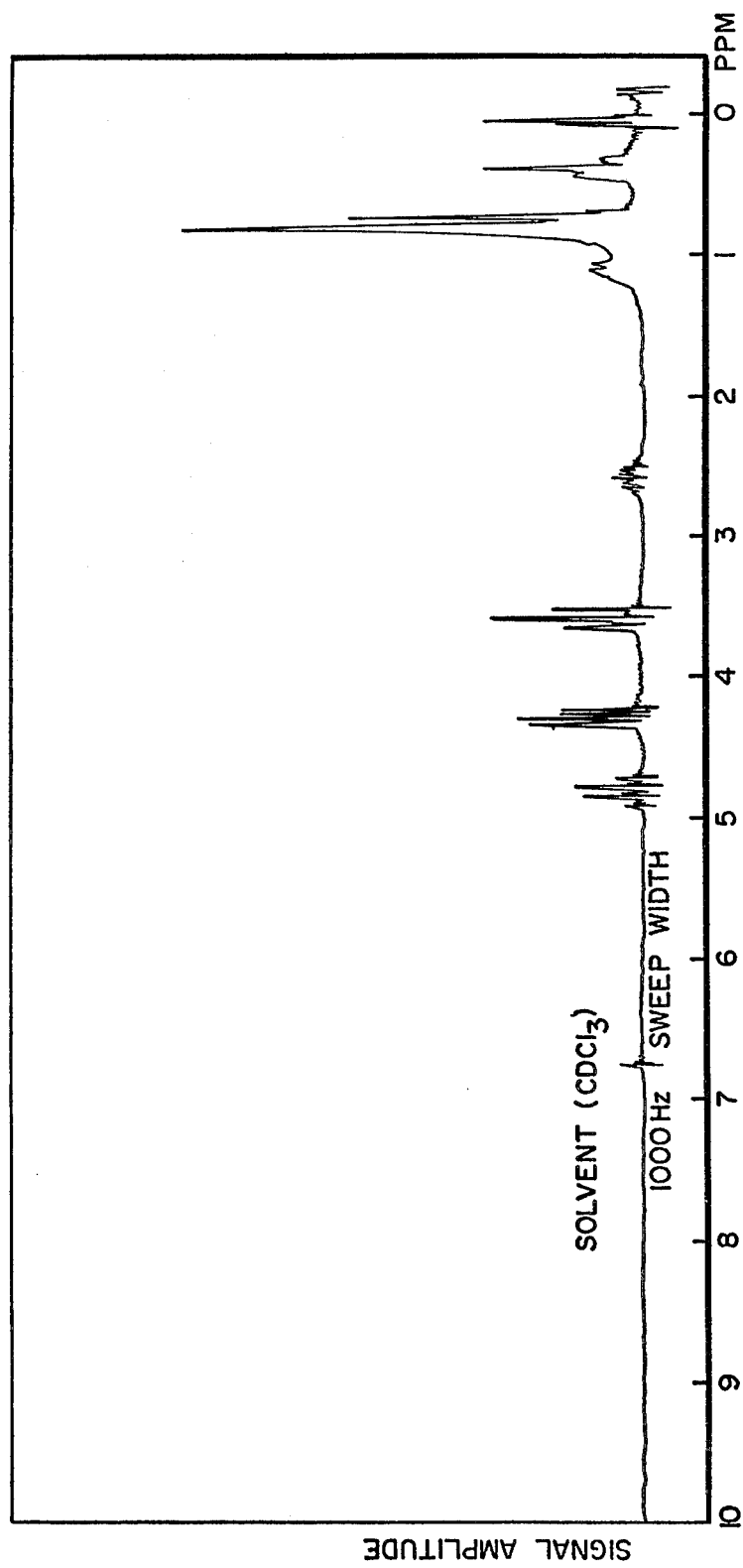
Figure 4:
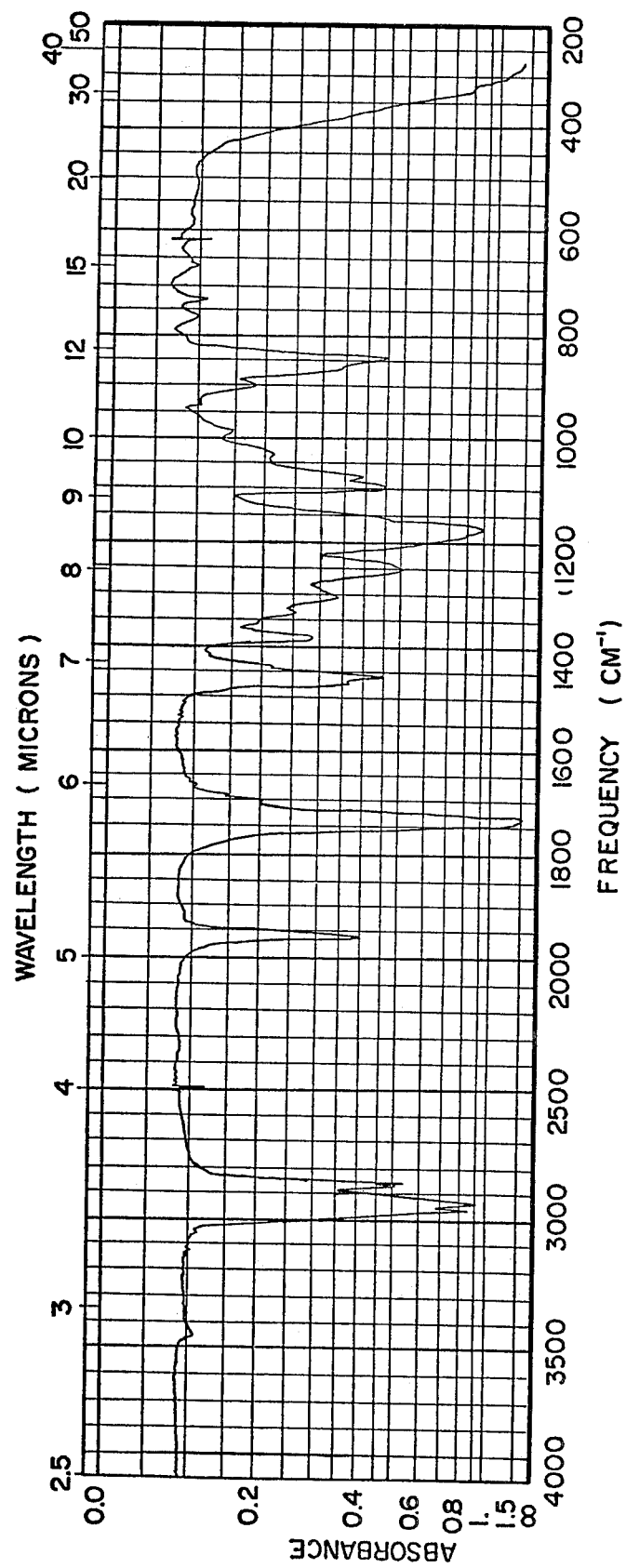

Analyses (1) The nuclear magnetic resonance spectrum is illustrated in FIG. 3.
(2) The infrared spectrum is illustrated in FIG. 4.
(3) Mass spectral analysis: Molecular ion; then in order of decreasing intensity: 196($M^+$); 43, 41, 112, 97, 67, 85.
(4) NMR analysis:

| ppm | Interpretation | |
|---|---|---|
| 0.88 ppm (t) | $CH_3-CH_2-$ | 3H |
| 1.24 ppm (d) | $CH_3-\underset{\underset{C=O}{\mid}}{\overset{\overset{C}{\mid}}{C}}-$ | |
| 1.28 (broad s) | $-CH_2-$ | 11H |
| 1.62 (m) | $-CH_2-C-O-$ | |
| 3.10 (m) | $=C-\underset{\mid}{\overset{H}{C}}-C=O$ | 1H |
| 4.08 (t) | $-CH_2-O-\overset{\overset{O}{\|}}{C}$ | 2H |
| 4.76 (7 doublets) | $H_2C=C=C-\left(\begin{array}{c}J = 3Hz\\6Hz\end{array}\right)$ | 2H |
| 5.32 (q) | $-C=C=CH$ | 1H |

(5) Infrared analysis:
845 $cm^{-1}$
1065
1085
1175
1250
1455
1730
1960
2860
2880
2940

2960

Insofar as its taste is concerned, the thus produced material has sweet, fruity, strawberry and tagette oil-like aroma and flavor notes with berry, pear and winey nuances. Insofar as its usefulness in perfumes is concerned, the thus produced material has a pear, green floral aroma with wormwood notes.

EXAMPLE XX

PREPARATION OF A COSMETIC POWDER COMPOSITION

A cosmetic powder is prepared by mixing in a ball mill, 100 g of talcum powder with 0.25 g of the n-hexyl-2-methyl-3,4-pentadienoate prepared according to Example XIX. It has an excellent long lasting fruity, apple, tagette-oil aroma with a chamomile nuance.

EXAMPLE XXI

PERFUMED LIQUID DETERGENT

Concentrated liquid detergents with a long lasting fruity, apple, tagette-oil odor are prepared containing 0.10%, 0.15% and 0.20% of hexyl-2-methyl-3,4-pentadienoate prepared according to Example XIX. They are prepared by adding and homogeneously mixing the appropriate quantity of n-hexyl-2-methyl-3,4-pentadienoate in the liquid detergent. The detergents all possess a fruity, apple, tagette-oil-like fragrance with a chamomile nuance, the intensity increasing with greater concentrations of n-hexyl-2-methyl-3,4-pentadienoate.

EXAMPLE XXII

PREPARATION OF A COLOGNE AND HANDKERCHIEF PERFUME

The product of Example XIX is incorporated in a cologne at a concentration of 2.5% in 85% aqueous ethanol; and into a handkerchief perfume at a concentration of 20% (in 95% aqueous ethanol). The use of the n-hexyl-2-methyl-3,4-pentadienoate of Example XIX affords a distinct and definite strong tagette-oil-like aroma with an apple note and a chamomile nuance to the handkerchief perfume and cologne.

EXAMPLE XXIII

PREPARATION OF SOAP COMPOSITION

One hundred grams of soap chips are mixed with one gram of n-hexyl-2-methyl-3,4-pentadienoate produced according to Example XIX until a substantially homogeneous composition is obtained. The perfumed soap composition manifests an excellent tagette-oil-like aroma with apple and chamomile nuances.

EXAMPLE XXIV

PREPARATION OF A DETERGENT COMPOSITION

A total of 100 g of a detergent powder is mixed with 0.15 g of the mixture containing n-hexyl-2-methyl-3,4-pentadienoate produced according to Example XIX until a substantially homogeneous composition is obtained. This composition has an excellent tagette-oil-like aroma with a chamomile nuance.

EXAMPLE XXV

PEAR FLAVOR FORMULATION CONTAINING n-HEXYL-2-METHYL-3,4-PENTADIENOATE

The following mixture is prepared:

| Ingredient | Parts by Weight |
|---|---|
| Vanillin | 2.0 |
| Ethyl hexanoate | 0.5 |
| Ethyl decanoate | 1.0 |
| Benzyl acetate | 0.5 |
| Ethyl octanoate | 2.0 |
| Gamma undecalactone 10% (in 95% ethyl alcohol) | 2.0 |
| Alpha ionone 0.1% (in 95% ethyl alcohol) | 5.0 |
| Hexyl acetate | 25.0 |
| Lemon oil, cold pressed | 5.0 |
| Ethyl butyrate | 7.0 |
| Ethyl acetate | 40.0 |
| Butyl acetate | 20.0 |
| Amyl valerate | 65.0 |
| Amyl acetate | 640.0 |
| Ethyl alcohol | 185.0 | n-hexyl-2-methyl-3,4-pentadienoate is added at the rate of 6% to a portion of the above basic pear formulation. The other portion is left "as is". Both flavors are compared in water at the rate of 50 ppm and evaluated by a bench panel to determine that the pear flavor with the addition of n-hexyl-2-methyl-3,4-pentadienoate has a fresh pear, winey, tagette oil-like aroma and a more full ripe pear, winey, slightly spicey taste. The pear formulation with the n-hexyl-2-methyl-3,4-pentadienoate is preferred because it provides basic notes missing in the basic pear flavor.

EXAMPLE XXVI

PREPARATION OF ISOBUTYL-2-METHYL-3,4-PENTADIENOATE

Reaction:

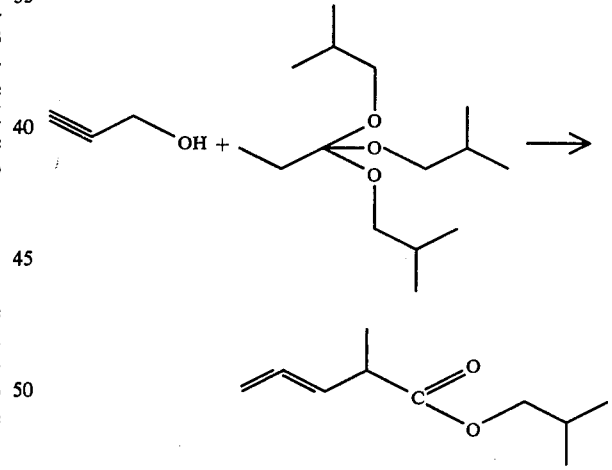

Into a 2 liter autoclave, the following materials are placed:

| Ingredient | Amount |
|---|---|
| Triisobutyl orthopropionate | 696.9 grams |
| 2-Propyn-1-ol | 151 grams |
| Propionic acid | 17 grams |

The autoclave is closed and the reaction mass is heated to 140° C over a period of 50 minutes. The reaction mass is then maintained at a temperature of 140° C for a period of 4 hours. At the end of this 4-hour period, the autoclave is opened and the reaction mass is cooled to room temperature. 20 g of sodium bicarbonate is then added to the reaction mass in order to neutralize the propionic acid. 30 g of Primol ® is added and the reaction mass is fractionally distilled on a 'inch splash column yielding the following fractions:

| Fraction No. | Vapor Temperature | Liquid Temperature | Pressure (mm Hg) | Weight of Fraction | % Product |
|---|---|---|---|---|---|
| 1 | 38-25° C | 45-27° C | 30-8.7 | 182.1 | 2 |
| 2 | 30 | 44 | 6.0 | 192.5 | 4.1 |
| 3 | 70 | 77 | 6.0 | 55.4 | 14.6 |
| 4 | 72 | 80 | 6.8 | 213.9 | 93.3 |
| 5 | 72 | 200 | 7.9 | 131.6 | 97 |

10 g Primol ® and 0.1 g Ionol ® are then added to the resulting distillate which is vacuum distilled yielding isobutyl-2-methyl-3,4-pentadienoate as follows:

| Fraction No. | Vapor Temperature | Liquid Temperature | Pressure (mm Hg) | Weight of Fraction | Reflux Ratio |
|---|---|---|---|---|---|
| 1 | 41-70° C | 77-83° C | 7.3-7.7 | 15.4 | 19:1-19:1 |
| 2 | 72 | 78 | 7.9 | 12.9 | 19:1 |
| 3 | 72 | 78 | 7.8 | 15.1 | 19:1 |
| 4 | 72 | 78 | 7.8 | 22.8 | 9:1 |
| 5 | 72 | 78 | 7.8 | 30.3 | 4:1 |
| 6 | 72 | 78 | 7.8 | 39.6 | 4:1 |
| 7 | 72 | 78 | 7.8 | 48.3 | 4:1 |
| 8 | 72 | 78 | 7.8 | 47.3 | 4:1 |
| 9 | 72 | 78 | 7.8 | 46.0 | 4:1 |
| 10 | 72 | 81 | 7.8 | 43.6 | 4:1 |
| 11 | 72 | 204 | 7.8 | 7.7 | 4:1 |

The resulting material is confirmed by NMR and IR analyses to have the structure:

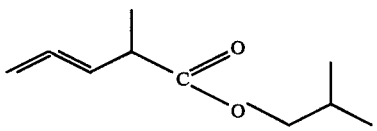

Nuclear Magnetic Resonance Analysis:

| ppm | Interpretation | |
|---|---|---|
| 0.92 ppm (d) | CH₃ H<br>     \\C—<br>CH₃ | 6H |
| 1.26 ppm (d) | C=C<br> \|<br>CH₃—CH<br>     \|<br>     C=O | 3H |
| 1.92 ppm (m) | H₃C  H<br>    \\ \|<br>     C—<br>H₃C | |
| 3.12 ppm (m) | O=C—C—C=C<br>         \|<br>         H | 1H |
| 3.87 ppm (d) | O<br>         \|\|<br>—CH₂—O—C— | 2H |
| 4.79 ppm (d of d) | H₂C=C=C—C | 2H |
| 5.33 ppm (m) | H₂C=C=C—C<br>           \|<br>           H | 1H |

The nuclear magnetic resonance spectrum is set forth in FIG. 5.

Infra Red Analysis
Peaks 840 cm⁻¹
985
1030
1065
1085
1170
1240
1300
1365
1375
1455
1470
1730
1955
2870
2940
2960

The infra-red spectrum is set forth in FIG. 6.

At 1 ppm this material has a winey and estery aroma and taste. At 2 ppm it has a fruity and sweet aroma and taste. At 5 ppm it is fruity and pineapple-like. At 10 ppm it has licorice-like notes, is winey.

What is claimed is:

1. A perfume composition comprising from 0.05% up to 5% by weight of the fragrance components of ethyl-2-methyl-3,4-pentadienoate having the structure:

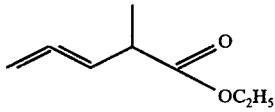

and the remainder of said composition being at least one adjuvant selected from the group consisting of natural perfume oils, synthetic perfume oils other than said ethyl-2-methyl-3,4-pentadienoate, alcohols, aldehydes, ketones, esters other than said ethyl-2-methyl-3,4-pentadienoate, lactones and nitriles.

2. A cologne composition comprising ethyl-2-methyl-3,4-pentadienoate having the structure:

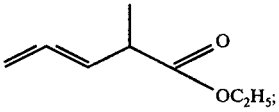

ethanol and water.

3. A perfume composition comprising from 0.05% up to 5% by weight of ethyl-2-methyl-3,4-pentadienoate and the remainder of said composition consisting essentially of at least one compound selected from the group consisting of:

Cuminic acetate;
Ethyl acetoacetate;
Ethyl laurate;
Cinnamyl isobutyrate;
Cinnamyl decylate;
Diacetyl;
Ethyl pelargonate;
Gamma undeclactone;
Ethyl isobutyrate;
Ethyl isovalerate;
Ethyl heptanoate;

Dulcinyl 2(para-hydroxyphenyl)-3-butanone;
Ethyl acetate;
Beta-ionone;
Palatone;
Vanillin;
Ethyl vanillin; and
Ethyl-3-methyl-3-phenyl glycidate;
the quantities of ingredients of said composition being in such amount that said perfume composition has a strawberry fragrance.

* * * * *